United States Patent [19]

Dickoré et al.

[11] 4,447,258
[45] May 8, 1984

[54] 3-DIMETHYLAMINO-4-METHYL-1,2,4-TRIAZIN-5(4H)-ONES AND HERBICIDAL COMPOSITIONS

[75] Inventors: Karlfried Dickoré, Leverkusen; Klaus Sasse, Bergisch-Gladbach; Ludwig Eue, Leverkusen; Robert R. Schmidt, Cologne, all of Fed. Rep. of Germany

[73] Assignee: Bayer Aktiengesellschaft, Leverkusen, Fed. Rep. of Germany

[21] Appl. No.: 120,174

[22] Filed: Feb. 11, 1980

[30] Foreign Application Priority Data

Mar. 7, 1979 [DE] Fed. Rep. of Germany ....... 2908963
Mar. 7, 1979 [DE] Fed. Rep. of Germany ....... 2908964
Sep. 22, 1979 [DE] Fed. Rep. of Germany ....... 2938384

[51] Int. Cl.³ .................. C07D 253/06; A01N 43/64
[52] U.S. Cl. ........................................ 71/93; 544/182
[58] Field of Search ............................ 544/182; 71/93

[56] References Cited

U.S. PATENT DOCUMENTS 3,544,570 12/1970 Timmler et al. .................. 544/182

FOREIGN PATENT DOCUMENTS 2138031 2/1973 Fed. Rep. of Germany.
2165554 7/1973 Fed. Rep. of Germany.
1577658 8/1969 France.

*Primary Examiner*—John M. Ford
*Attorney, Agent, or Firm*—Felfe & Lynch

[57] ABSTRACT

3-Dimethylamino-4-methyl-1,2,4-triazin-5(4H)-one compounds of the formula

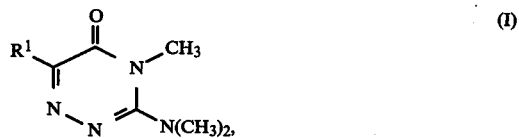

in which
$R^1$ is t-butyl, sec.-butyl or cyclohexyl;
are effective herbicides.

2 Claims, No Drawings

3-DIMETHYLAMINO-4-METHYL-1,2,4-TRIAZIN-5(4H)-ONES AND HERBICIDAL COMPOSITIONS

This invention relates to certain new triazinone compounds, more specifically to 6-substituted 3-dimethylamino-4-methyl-1,2,4-triazin-5(4H)-one compounds. In addition, the invention relates to herbicidal compositions containing such compounds and to methods of combating weeds utilizing such compounds.

It is known that certain 1,2,4-triazin-5(4H)-ones can be employed as agents for combating weeds. Thus it is known, for example, that certain 3-amino-substituted 4-alkyl-6-phenyl-1,2,4-triazin-5(4H)-ones, such as 3-N-morpholino-4-methyl-6-phenyl-1,2,4-triazin-5(4H)-one or 3-amino-4-methyl-6-phenyl-1,2,4-triazin-5(4H)-one can be used as herbicides (see DE-OS (German Published Specification) 1,670,912). However, the action of these preparations in low dosages is not always sufficient.

The present invention now provides, as new compounds, the 6-substituted 3-dimethylamino-4-methyl-1,2,4-triazin-5(4H)-ones of the general formula

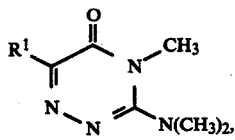

in which
R¹ represents a t-butyl group, a sec.-butyl group or a cyclohexyl group.

The triazinones of the formula (I) have powerful herbicidal properties. Surprisingly, the triazinone derivatives according to the invention display a considerably higher herbicidal action than the 3-amino-substituted 4-alkyl-6-phenyl-1,2,4-triazin-5(4H)-ones already known from the state of the art.

The invention also provides a process for the preparation of a triazinone of the formula (I) in which
(a) a 4-methyl-3-alkylthio-(or 3-aralkylthio)-triazin-5(4H)-one of the general formula

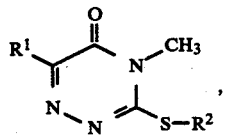

in which
R¹ has the meaning indicated above and
R² represents alkyl or aralkyl,
is reacted with dimethylamine, if appropriate in the presence of a diluent and if appropriate in the presence of a lower aliphatic carboxylic acid, or
(b) an α-ketocarboxylic acid of the general formula

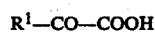

in which
R¹ has the meaning indicated above,
is reacted with a 3-amino-1,1,2-trimethylguanidinium salt of the general formula

in which
X represents Cl, Br or I,
in aqueous solution.

If, for example, 6-tert.-butyl-4-methyl-3-methylthio-1,2,4-triazin-5(4H)-one and dimethylamine are used as starting materials in process variant (a), the course of the reaction can be represented by the following equation:

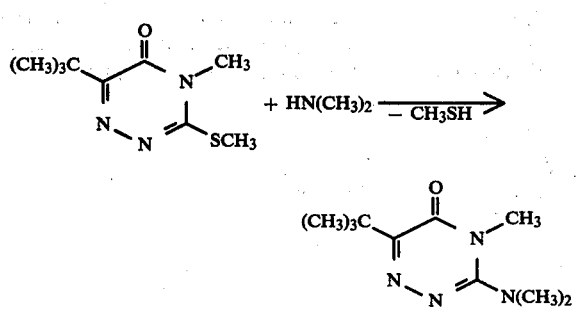

If cyclohexyl-glyoxylic acid and, for example, 3-amino-1,1,2-trimethyl-guanidinium hydriodide are used as starting materials in process variant (b), the course of the reaction can be represented by the following equation:

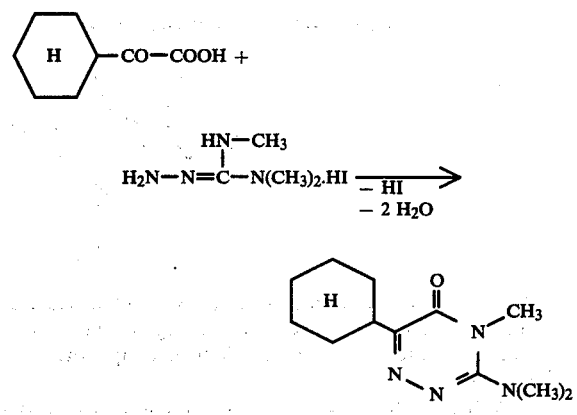

Most of the starting materials which can be used according to the invention are known. Thus, for example, the 6-tert.-butyl-4-methyl-3-methylthio-1,2,4-triazin-5(4H)-one (IIa) which can be used for process variant (a) has been prepared in 11% yield by N-methylating 6-tert.-butyl-3-methylthio-1,2,4-triazin-5(4H)-one (see Z. Naturf. 31 B, 1,122–1.126 (1976)). However it is more favourable to prepare this compound by S-methylation of 6-tert.-butyl-4-methyl-5-oxo-3-thioxo-tetrahydro-1,2,4(2H,4H)-triazine (V) (see the preparative examples given later in this text).

The 6-cyclohexyl-4-methyl-3-methylthio-1,2,4-triazin-5(4H)-one (IIc) which can be used for process variant (a) is known from DE-OS (German Published Specification) 1,670,912. This compound is prepared by S-methylation of 6-cyclohexyl-4-methyl-5-oxo-3-thioxo-tetrahydro-1,2,4(2H,4H)-triazine (VI). 6-sec.-butyl-4-methyl-3-methylthio-1,2,4-triazin-5(4H)-one (IIb), which has not hitherto been described in the literature, can be prepared in an analogous manner (see the preparative examples).

Other 6-tert.-butyl-, 6-sec.-butyl- and 6-cyclohexyl-3-alkylthio- or 3-aralkylthio-triazinones, for example the corresponding 3-ethylthio-, 3-propylthio, 3-benzylthio- or 3-(3-chlorobenzylthio)-triazinones, which are also suitable as starting materials for process variant (a), can be synthesised in a similar manner.

A process for the preparation of compound (VI) which can be carried out industrially is based on condensation of cyclohexanone with N-methylrhodanine to give cyclohexylidene-N-methylrhodanine (VII), which is hydrolysed under alkaline conditions to give 2-mercapto-2-cyclohexylidene-acetic acid (VIII). Condensation thereof with 4-methyl-thiosemicarbazide gives the compound (VI) (see the preparative examples):

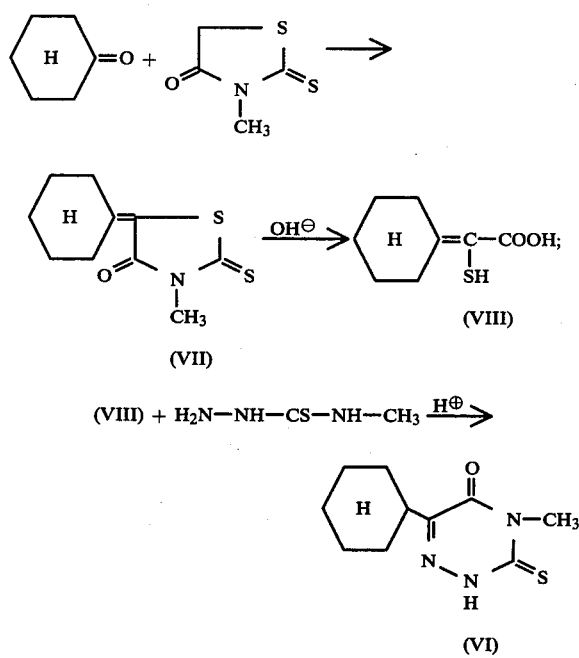

(VIII) + H$_2$N—NH—CS—NH—CH$_3$ $\xrightarrow{H^\oplus}$ (VI)

3,3-Dimethyl-2-oxo-butyric acid (IIIa) is known. This compound can be prepared industrially by the process indicated in DE-OS (German Published Specification) 2,648,300.

3-Methyl-2-oxo-valeric acid (IIIb) is likewise known (see Monatshefte f. Chemie 26, 483–495 (1905); and Beilsteins Handbuch der Organ. Chemie (Bielsteins Handbook of Organic Chemistry), 4th edition (1921), volume 3, page 690).

Cyclohexyl-glyoxylic acid (IIIc) is also known. This compound can be prepared, for example, by the process indicated in Liebigs Ann. Chem. 526 47–58 (1936).

3-Amino-1,1,2-trimethyl-guanidinium hydriodide (IV, X=I) can likewise be prepared by a process which is known from the literature (see J. Org. Chem. 19, 1,807–1,817 (1954)). The corresponding hydrochloride (IV, X=Cl) and hydrobromide (IV, X=Br) can be prepared in an analogous manner.

Possible diluents in process variant (a) are any of the inert organic solvents. These include hydrocarbons, such as toluene and xylene; chlorinated aromatic hydrocarbons, such as chlorobenzene, 1,2-dichlorobenzene and 1,2,4-trichlorobenzene; ethers, such as tetrahydrofuran and dioxan; alcohols, such as methanol, ethanol, propanol, and isopropanol; amides, such as N,N-dimethylformamide and tetramethylurea; or sulphoxides, such as dimethylsulphoxide. Isopropanol is preferably used for the reaction.

The reaction temperatures can be varied within a substantial range in process variant (a). In general, the reaction is carried out at a temperature from 20° to 170° C., preferably from 60° to 90° C.

The reaction can be carried out under normal pressure and also under increased pressures.

A particularly advantageous embodiment of process variant (a) consists in carrying out the reaction in the presence of at least an equimolar amount of a lower aliphatic carboxylic acid. Acetic acid is preferably used for this. This process enables a relatively small excess of dimethylamine to be used. In this embodiment, the rate of reaction can be increased by adding a catalytic amount of an organic sulphonic acid. p-Toluenesulphonic acid is preferably used for this.

In carrying out process variant (a) by this preferred process variant, 1 to 2 moles of a lower aliphatic carboxylic acid, 0.01 to 0.05 mole of an organic sulpho acid and 1 to 2 moles of dimethylamine are appropriately employed per mole of the 3-alkylthio- or 3-aralkylthio-triazinone of the formula (II), and the mixture is heated until the splitting off of the mercaptan has ended and is then worked up. This can be effected, for example, by a procedure in which the mixture is evaporated, the residue is stirred with excess aqueous mineral acid and insoluble impurities are separated off. The reaction product is precipitated in high purity by adding an excess amount of a base, for example ammonia.

Process variant (b) is carried out in aqueous solution. Appropriately, the sodium salt of the α-ketocarboxylic acid (III) is initially introduced in aqueous solution and, after adding the 3-amino-1,1,2-trimethylguanidinium salt (IV), the acid (III) is liberated by adding mineral acid, for example hydrochloric acid.

The reaction temperatures can likewise be varied within a substantial range in process variant (b). In general the reaction is carried out at a temperature of from 50° to 100° C., preferably from 65° to 90° C.

Process variant (b) is in general carried out under normal pressure.

In carrying out process variant (b), 1 to 1.1 moles of a 3-amino-1,1,2-trimethyl-guanidinium salt (IV) is employed per mole of the Na salt of the α-ketocarboxylic acid (III) in aqueous solution, and, after adding mineral acid, for example hydrochloric acid, the mixture is heated until the reaction has ended. Working up is then effected in the same manner as indicated for process variant (a).

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the general Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

In particular, in addition to a very good action against gramineaceous weeds, the active compounds according to the invention also exhibit a herbicidal action against broad-leaved weeds, especially also against species of Galium. It is possible to employ the active compounds according to the invention selectively, especially in maize, groundnut, soya bean, cotton, rice and other varieties of cereal.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with other herbicides, finished formulations or tank mixing being possible. Mixtures with other active compounds, such as fungicides, insecticides, acaricides, nematicides, bird repellents, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They may be used in the customary manner, for example by watering, spraying, atomising, dusting or scattering.

The active compounds according to the invention can be applied either before or after emergence of the plants. They are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are between 0.01 and 10 kg of active compound per ha, preferably between 0.1 and 5 kg/ha.

The present invention also provides a herbicidal composition containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The herbicidal activity of the compounds of this invention is illustrated by the following biotest Examples.

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:
  0% = no action (like untreated control)
  100% = total destruction In this test, the active compounds (Ia), (Ib) and (Ic) exhibit an excellent action.

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amount of active compound desired per unit area. The concentration of the spray liquor is so chosen that the particular amount of active compound desired is applied in 2,000 l of water/ha. After three weeks, the degree of damage to the plants is rated in % damage in comparison to the development of the untreated control. The figures denote:
  0% = no action (like untreated control)
  100% = total destruction In this test also, the active compounds (Ia), (Ib) and (Ic) exhibit an outstanding action.

PREPARATIVE EXAMPLES

Example 1

6-tert.-Butyl-3-dimethylamino-4-methyl-1,2,4-triazin-5(4H)-one (Ia)-process variant (a)

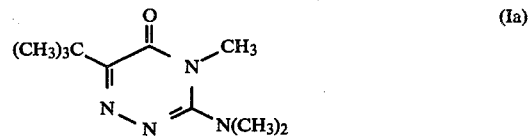

1,850 g of acetic acid and 125 g of p-toluene-sulphonic acid were initially introduced into 15 liters of isopropanol. 1,800 g of dimethylamine were passed in, whilst cooling, 5,250 g (24.65 mol) of 6-tert.-butyl-4-methyl-3-methylthio-1,2,4-triazin-5(4H)-one were then added and the mixture was heated under reflux until the evolution of methylmercaptan had ended. Most of the solvent was then distilled off at an internal temperature of 80°–90° C., whilst passing nitrogen through.

The oily residue was stirred with 25 liters of 5% strength hydrochloric acid and 2 liters of chloroform at 0°–5° C. The organic phase was separated off and discarded. 3 liters of 25% strength ammonia solution were added to the aqueous phase, whilst cooling, whereupon the reaction product precipitated as crystals. The crystals were filtered off at 0° C., washed with a little ice-water and dried at 50° C.

4,438 g (86% of theory) of the compound (Ia) shown above of melting point 89°–91° C. were obtained. The purity, determined by gas chromatography, was greater than 99%. The compound could be distilled: boiling point: 115° C./0.03 mbar.

Example 2

6-sec.-Butyl-3-dimethylamino-4-methyl-1,2,4-triazin-5(4H)-one (Ib)-process variant (a)

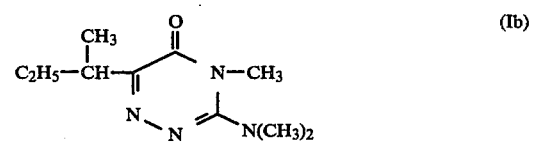

1,065 g (5 mol) of 6-sec.-butyl-4-methyl-3-methylthio-1,2,4-triazin-5(4H)-one, 375 g of acetic acid and 25 g of p-toluenesulphonic acid were initially introduced into 3 liters of isopropanol. 360 g (8 mol) of dimethylamine were passed in, without cooling, the mixture was boiled under reflux for 6 hours and a further 225 g (5 mol) of dimethylamine were then passed into the boiling mixture in the course of 6 hours. Most of the solvent was first distilled off under normal pressure at 90°–100° C., whilst passing nitrogen through; residual amounts of the solvent were then removed under 20 mbars and at a bath temperature of 100° C.

The oily residue was stirred with 6 liters of ice-water and 460 ml of 37% strength hydrochloric acid at 0°–5° C., 400 ml of chloroform were added and, after stirring the mixture thoroughly for a short time, the phases were separated. The organic phase was discarded; 2 liters of 25% strength ammonia solution were added to the aqueous phase at 10°–20° C., whilst stirring, the oil which had separated out was taken up in 400 ml of chloroform, the phases were separated, the aqueous phase was extracted by stirring once more with 400 ml of chloroform and the evaporation residue of the combined chloroform solutions was distilled under a high vacuum.

892 g (85% of theory) of the compound (Ib) shown above of boiling point 131° C./0.15 mbar and with the refractive index $n_D^{20}=1.5324$ were obtained.

The purity, determined by gas chromatography, was 99%.

Example 3

6-Cyclohexyl-3-dimethylamino-4-methyl-1,2,4-triazin-5(4H)-one (Ic)-process variant (a)

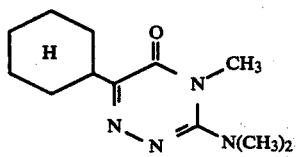

1,850 g of acetic acid and 125 g of p-toluene-sulphonic acid were initially introduced into 15 liters of isopropanol. 1,800 g of dimethylamine were passed in, whilst cooling, 5,850 g (24.48 mol) of 6-cyclohexyl-4-methyl-3-methylthio-1,2,4-triazin-5(4H)-one were then added and the mixture was heated under reflux until the evolution of methylmercaptan had ended. Most of the solvent was then distilled off at an internal temperature of 80°-90° C., whilst passing nitrogen through.

The oily residue was stirred with 25 liters of 5% strength hydrochloric acid and 2 liters of chloroform at 0°-5° C. The organic phase was separated off and discarded. 3 liters of 25% strength ammonia solution were added to the aqueous phase, whilst cooling, whereupon the reaction product precipitated as crystals. The crystals were filtered off at 0° C., washed with a little ice-water and dried at 50° C.

4,740 g (82% of theory) of the compound (Ic) shown above of melting point 104°-106° C. were obtained.

STARTING MATERIALS (a)
6-tert.-Butyl-4-methyl-5-oxo-3-thioxo-tetrahydro-1,2,4(2H,4H)-triazine

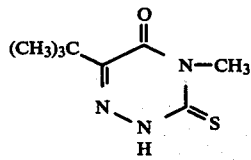

4,725 g (45 mol) of 4-methyl-thiosemicarbazide were dissolved in 25 liters of water and 6 liters of 35% strength hydrochloric acid; 92 liters, containing 46 moles, of an aqueous solution of the Na salt of 3,3-dimethyl-3-oxo-butyric acid were added, whilst stirring, and the mixture was boiled under reflux for 10 hours. The product was filtered off at 50° C., washed with water and dried at 80° C. 7,340 g (82% of theory) of the compound (V) of melting point 214° C. were obtained.

(b)
6-tert.-Butyl-4-methyl-3-methylthio-1,2,4-triazin-5(4H)-one

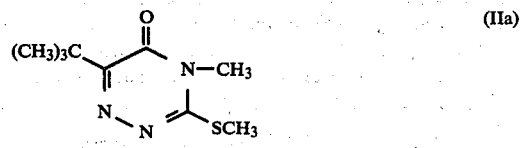

30 ml of 3-benzyl-4-hydroxy-biphenyl polyglycol ether, as an emulsifier, and 5,690 g (28.6 mol) of 6-tert.-butyl-4-methyl-5-oxo-3-thioxo-tetrahydro-1,2,4-(2H,4H)-triazine were added to a solution of 1,145 g of NaOH in 57 liters of water. 4,302 g (30.3 mol) of methyl iodide were added dropwise (or 2,900 g of methyl bromide were passed in) and the mixture was subsequently stirred until the slightly exothermic reaction had ended and the pH value had reached 7-8. After filtering off the product, washing it with water and drying it at 50° C., 5,810 g (95% of theory) of the compound (IIa) of melting point 90°-100° C. were obtained. The crude product was sufficiently pure for further reaction. A sample recrystallised from methanol or petroleum ether melted at 104°-105° C.

(c)
6-sec.-Butyl-4-methyl-5-oxo-3-thioxo-tetrahydro-1,2,4(2H,4H)-triazine

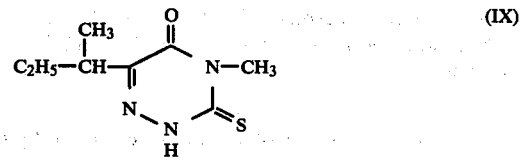

525 g (5 mol) of 4-methyl-thiosemicarbazide were dissolved in 2 liters of water and 600 ml of 37% strength hydrochloric acid and a solution of 760 g (5 mol) of the Na salt of 3-methyl-2-oxo-valeric acid in 1.5 liters of water was added rapidly at 95°-100° C. The mixture was boiled under reflux for 10 hours and left to cool, whilst stirring, and the product was filtered off and washed with 2 liters of water. The moist crude product was then stirred with 1 liter of methanol at −20° C., filtered off at −20° C. and washed with methanol at −70° C. After drying at 80° C., 697 g (70% of theory) of the compound (IX) of melting point 117°-119° C. were obtained. A sample recrystallised from methanol melted at the same temperature.

(d)
6-sec.-Butyl-4-methyl-3-methylthio-1,2,4-triazin-5(4H)-one

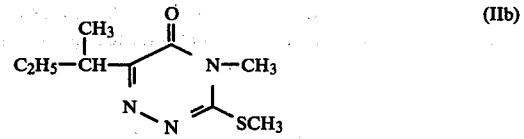

1 ml of 3-benzyl-4-hydroxy-biphenyl polyglycol ether, as an emulsifier, and 995 g (5 mol) of 6-sec.-butyl-4-methyl-5-oxo-3-thioxo-tetrahydro-1,2,4(2H,4H)-triazine (IX) were added to a solution of 202 g of NaOH in 5 liters of water. 724 g (5.1 mol) of methyl iodide were added dropwise and the mixture was subsequently stirred until the slightly exothermic reaction had ended and the pH value had reached 7-8. After filtering off the product, washing it with water and drying it at 30° C. in vacuo, 907 g (85% of theory) of the compound (IIb) of melting point 45°-50° C. were obtained. The crude product was sufficiently pure for further reaction. A sample recrystallised from pentane melted at 54°-55° C.

(e) Cyclohexylidene-N-methyl-rhodanine

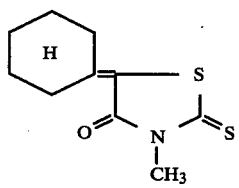

(VII)

4,807 g (32.7 mol) of N-methylrhodanine were suspended in 19.6 liters of methanol, 6,420 g (65.4 mol) of cyclohexanone were added and the mixture was warmed to 50° C., whilst stirring. 570 g (6.54 mol) of morpholine were then added dropwise, without further heating, whereupon the starting material dissolved and an exothermic reaction proceeded. After a short time, compound (VII) started to precipitate as light yellow crystals. When the exothermic reaction had ended, the mixture was boiled for a further hour under reflux and the product was filtered off at 20° C. and washed several times with methanol. 7,190 g (97% of theory) of the compound (VII) of melting point 111°-113° C. were obtained.

(f) 6-Cyclohexyl-4-methyl-5-oxo-3-thioxo-tetrahydro-1,2,4(2H,4H)-triazine

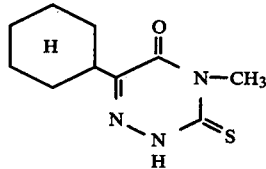

(VI)

7,180 g (31.6 mol) of cyclohexylidene-N-methylrhodanine were suspended in a solution of 6,326 g of sodium hydroxide in 60 liters of water and the suspension was stirred at 60° C. for 10 hours. After this time, virtually everything had dissolved. Insoluble residues were removed by extraction by stirring with 2 liters of chloroform. After separating off the organic phase, 3,320 g (31.6 mol) of 4-methyl-thiosemicarbazide were introduced into the resulting aqueous solution of the Na salt of 2-mercapto-2-cyclohexylidene-acetic acid (VIII), the mixture was heated to 80° C. and 19.0 liters of 32% strength hydrochloric acid were added dropwise. A condensation reaction to give compound (VI) took place, with evolution of H₂S. The reaction product was filtered off at 60° C. and washed several times with water and, after drying at 80° C., 5,830 g (82% of theory) of the compound shown above of melting point 173°-176° C. were obtained. A sample recrystallised from chlorobenzene melted at 186° C.

(g) 6-Cyclohexyl-4-methyl-3-methylthio-1,2,4-triazin-5(4H)-one

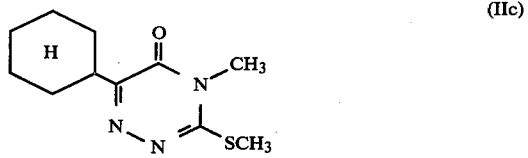

(IIc)

30 ml of 3-benzyl-4-hydroxy-biphenyl polyglycol ether, as an emulsifier, and 5,805 g (25.8 mol) of 6-cyclohexyl-4-methyl-5-oxo-3-thioxo-tetrahydro-1,2,4-(2H,4H)-triazine were added to a solution of 1,033 g of NaOH in 52 liters of water. 3,881 g (27.3 mol) of methyl iodide were added dropwise (or 2,620 g of methyl bromide were passed in) and the mixture was subsequently stirred until the slightly exothermic reaction had ended and the pH value had reached 7-8. After filtering off the product, washing it with water and drying it at 50° C., 5,860 g (95% of theory) of the compound (IIc) of melting point 84°-88° C. were obtained. The crude product was sufficiently pure for further reaction. A sample recrystallized from methanol or petroleum ether melted at 90° C.

It will be understood that the specification and examples are illustrative but not limitative of the present invention and that other embodiments within the spirit and scope of the invention will suggest themselves to those skilled in the art.

What is claimed is:

1. 3-Dimethylamino-4-methyl-1,2,4-triazin-5(4H)-one compound designated 6-tert.-butyl-3-dimethylamino-4-methyl-1,2,4-triazin-5(4H)-one of the formula

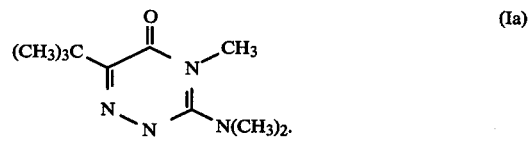

(Ia)

2. Method of combating setaria, sinapis, matricaria, galinsoga, stellaria, lolium, echinochloa, wheat, oats, cotton and maize which method comprises applying to such vegetation or its habitat a herbicidally effective amount of a 3-dimethylamino-4-methyl-1,2,4-triazin-5(4H)-one compound as claimed in claim 1.

* * * * *